(12) United States Patent
Messier et al.

(10) Patent No.: US 10,918,103 B2
(45) Date of Patent: Feb. 16, 2021

(54) ANTITOXIC FIBERS

(71) Applicant: I3 Biomedical Inc., Mirabel (CA)

(72) Inventors: Pierre Jean Messier, Mirabel (CA); David Ohayon, Dollard-des-Ormeaux (CA)

(73) Assignee: I3 Biomedical Inc., Quebec (CA)

( * ) Notice: Subject to any disclaimer, the term of this patent is extended or adjusted under 35 U.S.C. 154(b) by 0 days.

(21) Appl. No.: 13/908,210

(22) Filed: Jun. 3, 2013

(65) Prior Publication Data

US 2013/0323290 A1    Dec. 5, 2013

Related U.S. Application Data

(60) Provisional application No. 61/735,388, filed on Dec. 10, 2012, provisional application No. 61/654,325, (Continued)

(51) Int. Cl.
*A01N 25/34* (2006.01)
*D06M 11/50* (2006.01)
(Continued)

(52) U.S. Cl.
CPC .............. *A01N 25/34* (2013.01); *A61L 15/44* (2013.01); *A61L 31/16* (2013.01); *D06M 11/09* (2013.01);
(Continued)

(58) Field of Classification Search
CPC .... A01N 59/12; A01N 2300/00; A01N 33/12; A01N 25/34; A01N 25/02; A01N 25/08;
(Continued)

(56) References Cited

U.S. PATENT DOCUMENTS 4,391,605 A * 7/1983 Bakker ................ D06M 13/46
                                                    252/8.61
4,443,573 A * 4/1984 Wells .................. B29C 47/1063
                                                    524/308
(Continued)

FOREIGN PATENT DOCUMENTS

DE          20122630 U1    11/2006
EP          2458083 A2      5/2012
(Continued)

OTHER PUBLICATIONS

Singhal et al. "Antibacterial multifilament nylon sutures", Biomat., Art. Cell & Biotech., 19 (3), 631-648 (1991).*
(Continued)

*Primary Examiner* — Isis A Ghali
(74) *Attorney, Agent, or Firm* — Betsy Kingsbury Dowd, Esq.; BKDowd Law, P.C.

(57) ABSTRACT

Antitoxic fibers and fibrous media contain impregnated material including an antitoxin. A method for producing antitoxic fibers and fibrous media includes impregnating a fibrous media by dipping in a dipping solution containing a concentrate of an antitoxin to form a fiber with impregnated material including an antitoxin. The impregnated material is at least about 1.0% to about 2.5% by weight of the fibers and includes additive chemical components including at least one of an anionic, cationic or nonionic component, an oil and/or an organic solvent, and an alcohol. The additives include those found in a spin finish. The antitoxin is in an amount of at least 0.1% by weight of the fiber. The manufacturing process can be applied to any woven or nonwoven media. Products with antitoxic properties formed therefrom include wound dressings, gowns, articles of clothing, surgical drapes, protective clothing, shoe covers, gloves, hair
(Continued)

| LOG reduction (LOG/mL) | | | |
|---|---|---|---|
| Material status | Contact time | Old technology 2.0 GSM of iodine (n=9) | New technology o,4 GSM of iodine (n=3) |
| Lot# | | 071410-1-FDA | Sept 2011 |
| Fresh | 15 minutes | 3.77 | >4.98 |
| Test ID | | M150710 | M060911-1 |
| Aged 2 months at Room Temp. | 15 minutes | 0.52 | 4.66 | covers, air filters, including facemasks, privacy, hygienic products, curtains, medical tape, and wipes.

15 Claims, 9 Drawing Sheets

Related U.S. Application Data filed on Jun. 1, 2012, provisional application No. 61/654,406, filed on Jun. 1, 2012.

(51) Int. Cl.
| | |
|---|---|
| *D06M 16/00* | (2006.01) |
| *A61L 31/16* | (2006.01) |
| *D06M 11/09* | (2006.01) |
| *A61L 15/44* | (2006.01) |

(52) U.S. Cl.
CPC ............ *D06M 11/50* (2013.01); *D06M 16/00* (2013.01); *A61L 2300/106* (2013.01); *A61L 2300/202* (2013.01)

(58) Field of Classification Search
CPC .... A01N 25/30; A01N 25/14; A61K 2300/00; A61K 33/18; A61K 9/7007
See application file for complete search history.

(56) References Cited

U.S. PATENT DOCUMENTS

| | | | |
|---|---|---|---|
| 4,933,236 A | 6/1990 | Anderson et al. | |
| 4,999,190 A | 3/1991 | Fina et al. | |
| 6,093,602 A | 4/2000 | Caldwell et al. | |
| 6,077,468 A * | 6/2000 | Jariwala | D06M 7/00 264/103 |
| 6,429,183 B1 * | 8/2002 | Leonard et al. | 510/438 |
| 7,491,753 B2 * | 2/2009 | Krishnan | A01N 25/10 523/122 |
| 2002/0155149 A1 * | 10/2002 | Gottlund | A01N 59/12 424/446 |
| 2003/0175438 A1 | 9/2003 | Reeve | |
| 2003/0194447 A1 * | 10/2003 | Scholz et al. | 424/672 |
| 2005/0147657 A1 | 7/2005 | Canada et al. | |
| 2006/0051384 A1 | 3/2006 | Scholz et al. | |
| 2006/0144403 A1 | 7/2006 | Messier | |
| 2008/0207794 A1 * | 8/2008 | Wright | D01D 5/00 522/183 |
| 2010/0074858 A1 * | 3/2010 | Messier | A01N 59/12 424/78.1 |
| 2010/0080993 A1 * | 4/2010 | Privitera | D01D 5/0038 428/401 |
| 2010/0136079 A1 * | 6/2010 | Kelly et al. | 424/409 |
| 2010/0176051 A1 * | 7/2010 | Shimagaki | B01J 20/26 210/437 |
| 2013/0053479 A1 * | 2/2013 | Bond | C08K 5/0008 524/57 |

FOREIGN PATENT DOCUMENTS

| | | |
|---|---|---|
| JP | H09132867 A * | 5/1997 |
| WO | WO2002079563 A1 | 10/2002 |
| WO | WO2010144503 A2 | 12/2010 |
| WO | 2011103578 | 8/2011 |
| WO | WO 2012002943 A1 * | 1/2012 |
| WO | WO2013086511 A1 | 6/2013 |

OTHER PUBLICATIONS

International Search Report dated Oct. 24, 2013.
Onar N Etal, "Antimicrobial, UV-protective and self-cleaning properties of cotton fabrics . . . ", Fibers and Polymers, The Korean Fiber Society, Heidelberg, Jun. 22, 2011, pp. 461-470.
Labor Teks, "Pneumatic type heavy duty padding mangle," http://ttrapid.com/pdf/air_pad.pdf, Jan. 1, 2000, pp. 1-4.
M P Sathianarayanan et al., "Antibacterial finish for cotton fabric from herbal products," Indian Journal of Fibre & Textile Research, Mar. 1, 2010,pp. 50-58.
Kjaerheim V, et al., "Organic solvents and oils as vehicles for triclosan in mouthrinses: a clinical study," Scand. J. Dent. Res., Oct. 1994; 102(5):306-8, Abstract.
Material Safety Data Sheet for Mililube N-29, Goulston Surface Modificiation Technologies, Mar. 2015.
ASTM E2149-01, "Standard Test Method for Determining the Antimicrobial Activity of Immobilized Antimicrobial Agents Under Dynamic Contact Conditions," ASTM (Aug. 2001).
ASTM D1909-04, "Standard Table of Commercial Moisture Regains for Textile Fibers," ASTM (Mar. 2004).

* cited by examiner

FIGURE 1

Comparative Antimicrobial Efficacy against Gram-Negative Bacteria
TrioMed Curtains vs. Currently Available Commercial Curtains Test Method: ASTM 2149

| Contact Time | TrioMed | Log Reduction Product A | Product B | |
|---|---|---|---|---|
| 5 min | >4.54 | 0.28 | 3.17 | *Acinetobacter baumannii* |
| 15 min | >4.54 | 0.82 | >3.71 | |

| Contact Time | TrioMed | Log Reduction Product A | Product B | |
|---|---|---|---|---|
| 5 min | >4.50 | N/A | >3.97 | *Pseudomonas aeruginosa* |
| 15 min | >4.50 | 0.34 | >3.97 | |

| Contact Time | TrioMed | Log Reduction Product A | Product B | |
|---|---|---|---|---|
| 5 min | >4.13 | 0.01 | 1.83 | *Salmonella enterica* |
| 15 min | >4.13 | 0.02 | 3.56 | |

FIGURE 2
Summary of Comparative Antimicrobial Efficacy

| Microbial Class/Microorganism | Contact Time | Log Reduction | | |
|---|---|---|---|---|
| | | Product B | Product A | TrioMed |
| Gram-Positive Bacteria | | | | |
| S. aureus MRSA | 5 min | 1.25 | N/A | 4.20 |
| S. aureus | 5 min | 2.68 | 0.34 | >4.46 |
| E. faecalis VRE | 5 min | 1.46 | 0.06 | >4.04 |
| E. hirae | 5 min | 0.11 | 0.07 | 3.49 |
| Gram-Negative Bacteria | | | | |
| A. baumannii | 5 min | 3.17 | 0.28 | >4.54 |
| P. aeruginosa | 5 min | >3.97 | 0.34 | >4.50 |
| S. enterica | 5 min | 1.83 | 0.01 | >4.13 |
| Bacterial Spores | | | | |
| C. difficile | 24 hrs | 0.08 | 0.04 | 1.29 |
| Viruses | | | | |
| Influenza A H1N1 | 15 min | 0.56 | 1.53 | 5.37 |

| LOG reduction (LOG/mL) | | | |
|---|---|---|---|
| Material status | Contact time | Triosyn/Simalfa scrim (n=9) | Triomed Active Scrim (n=3) |
| Lot# | | 071410-1-FDA | 040412-mid #4 |
| Fresh | 15 minutes | 3.77 | >4.92 |
| Test ID | | M150710 | M100412 |
| Fresh & Simulated usage 6 hours | 15 minutes | 0.59 | >4.92 |

FIGURE 3

| LOG reduction (LOG/mL) | | | |
|---|---|---|---|
| Material status | Contact time | Old technology 2.0 GSM of iodine (n=9) | New technology o,4 GSM of iodine (n=3) |
| Lot# | | 071410-1-FDA | Sept 2011 |
| Fresh | 15 minutes | 3.77 | >4.98 |
| Test ID | | M150710 | M060911-1 |
| Aged 2 months at Room Temp. | 15 minutes | 0.52 | 4.66 |

FIGURE 4

Fig. 5 Antimicrobial Properties of
TrioMed Active Disposable Hospital Privacy Curtains using AATCC Test Method 100-2004:
Assessment of Antibacterial Finishes on Textile Materials %Reduction of *P.aeruginosa* challenged on Aged TrioMed Active Curtain Fabrics:
Aged at 50° C from 0 to 25 days (0 to 1yrs. at Room Temp.)

| Days at 50° C | Aged yrs at Room Temp. | $I_2$ ppm | %Reduction* |
|---|---|---|---|
| 0 | 0 | 2.75 | >99.9994% |
| 12 | 0.5 | 2.63 | >99.9997% |
| 20 | 0.8 | 2.30 | >99.9997% |
| 25 | 1.0 | 2.03 | >99.9998% |

*Summary of AATCC 100 Test Method:
1- Expose Antimicrobial-treated Swatches to liquid microbial suspension (100 ml)
2- Wait for 15 minute contact time
3- Place sample in neutralizing fluid to recover viable microorganisms
4- Count viable microorganisms (CFU)

Fig. 6 Antimicrobial Properties of
TrioMed Active Disposable Hospital Privacy Curtains using AATCC Test Method 100-2004:
Assessment of Antibacterial Finishes on Textile Materials %Reduction of *P.aeruginosa* challenged on Aged Blue Active Curtain Fabrics: Aged at 50° C from 0 to 25 days (0 to 1yrs. at Room Temp.)

| Days at 50° C | Aged yrs at Room Temp. | $I_2$ ppm | %Reduction* |
|---|---|---|---|
| 0 | 0 | 3.14 | >99.9998% |
| 12 | 0.5 | 2.82 | >99.9998% |
| 20 | 0.8 | 1.79 | >99.9996% |
| 25 | 1.0 | 1.82 | >99.9996% |

*Summary of AATCC 100 Test Method:
1- Expose Antimicrobial-treated Swatches to liquid microbial suspension (100 ml)
2- Wait for 15 minute contact time
3- Place sample in neutralizing fluid to recover viable microorganisms
4- Count viable microorganisms (CFU)

Fig. 7 Antimicrobial Properties of
TrioMed Active Disposable Hospital Privacy Curtains using AATCC Test Method 100-2004:
Assessment of Antibacterial Finishes on Textile Materials

| %Reduction of *P.aeruginosa* challenged on wetted Blue TrioMed Active Curtain Fabrics: | | |
|---|---|---|
| Exposure to Wet glove contact treatment | | |
| Contact time | $I_2$ ppm | %Reduction* |
| 15 | 1.60 | >99.9996% |

*Summary of Wet Glove Treatment used:
1. Prepare the TrioMed Active Curtain Stack and place on flat surface
2. With a surgical glove on a hand, immerse in water
3. Hold glove up so that the excess water on the surface will dip off
4. Use the wet gloved hand and rub against the top surface of the TrioMed Active Curtain Stack
5. Repeat steps 2 to 4 for a total of 5 rubs and then let dry Fig. 8 Assessment of Iodine and Iodine Related Species on TrioMed Active Fabric Iodine species analysis on TrioMed Active Media: Yellow, White, and Yellow Regenerated Media

| Media | $I_2$ ppm | $I_3^-$ ppm | $IO_3^-$ ppm | HIO ppm | $I^-$ ppm |
|---|---|---|---|---|---|
| Yellow | 0.94 | 3.61 | 0.31 | 0.40 | 2.84 |
| White | BDL* | 3.05 | 0.76 | 0.90 | 2.71 |
| Regenerated Yellow | 0.98 | 3.21 | 0.16 | 0.24 | 3.21 |

*BDL = Below the limit of detection of 0.1ppm

Summary of Analysis:
1- Samples were prepared and analyzed as indicated in "*Spectrophotometric Determination Of Inorganic Iodine Compounds And Hydrogen Peroxide In Neutral And Slightly Alkaline Solutions*" by A. Habersbergerová

Fig. 9 Antimicrobial Properties of
TrioMed Active Disposable Hospital Privacy Curtains using AATCC Test Method 100-2004:
Assessment of Antibacterial Finishes on Textile Materials %Reduction of *P.aeruginosa* challenged on Blue Active Curtain Fabrics:
Fabrics produced at varying roll speeds

| Roll speed (ft/min) | $I_2$ ppm | %Reduction |
|---|---|---|
| 12 | 0.47 | >99.9995% |
| 8 | 1.47 | >99.9995% |
| 6 | 1.46 | >99.9995% |
| 4.8 | 1.13 | >99.9995% |

Production of the Material:
The Blue Active Curtain Fabric was produced on a line at varying speeds through a diptank containing a iodine solution with spin finish.

ANTITOXIC FIBERS

CROSS REFERENCE TO RELATED APPLICATIONS

This application claims priority to co-pending U.S. Provisional Application Nos. 61/654,325 filed Jun. 1, 2012; 61/654,406 filed Jun. 1, 2012; and 61/735,388 filed Dec. 10, 2012, the entirety of each of which is incorporated herein by reference thereto.

FIELD OF THE DISCLOSURE

The present disclosure relates to antitoxic fibers and fibrous media and methods for their manufacture, most particularly, to methods for impregnating or molecularly grafting antitoxins onto and into fibers and media formed therefrom. The disclosure also relates to products comprising the antitoxic fibers and fabrics so formed.

BACKGROUND

Various methods for producing antimicrobials and other antitoxins for use in both nonwoven and woven fabrics are known. However, improvements in the production of antitoxins or antimicrobials and in the products that incorporate them, so that they exhibit both low toxicity and high efficacy, are still needed.

The terms antitoxin and antitoxic as used herein include any antimicrobial, anti-chemical, chemical reducer, antifungal, and antiviral agent.

A woven or nonwoven material can be loaded with antitoxin in different ways and at different points during or after processing of the material. For example, an antitoxic agent can be embedded in fibers of a nonwoven, incorporated into the interstitial spaces of a material, or glued or sprayed onto an outer layer of a fabric following production. The method of incorporation and the location of the antitoxic agent in the material may have important consequences in imparting the desired efficacy and toxicology to the material and resultant product.

In the case of nonwoven materials, for example, one method involves physically entrapping the active agent within the three-dimensional structure of the nonwoven material. The active agent must have the appropriate size to be entrapped within the matrix structure of the nonwoven web. For instance, U.S. Publication No. 2006/0144403 (the '403 publication), to Messier, describes several methods of physically entrapping an active agent such as an iodine demand disinfectant resin in a three-dimensional nonwoven matrix. The '403 publication is hereby incorporated by reference in its entirety. Another method involves making use of a meltblown system where the desired active agent is provided in a cloud at the location after the extrusion point of the fibers when it is in a solid state. The cloud of active agent envelops the extruded fibers exiting a spinneret. The active agent becomes physically entrapped by the fibers on the collecting web.

In addition to physically entrapping the active agent, certain methods of incorporating the active agent or antitoxin directly into the fiber are known. Generally, the active agent is blended (compounded) with the polymer prior to extrusion so that it is present throughout the polymer. Upon solidification of the polymer, the active agent is dispersed throughout the resultant fiber. The active agent may diffuse to the surface of the nonwoven, where it exerts its toxic effect on the microorganism/toxin. For example, the '403 publication describes a method in which polymer granules are placed in a hopper along with active agent in powder form, preferably an iodine/resin disinfectant, prior to extrusion. The two components are then heated, extruded and attenuated to form fibers having the active agent incorporated therein. The resulting fibers having the active agent embedded can be carded, air laid, vacuum laid or water laid. Nonwoven materials generated from this process can be utilized in various applications.

Although methods described above produce efficacious materials, a significant loss of the antitoxic agent may be encountered during the various processing steps. In the meltblown procedure, for instance, it is found that the steps of heating and extrusion may result in sublimation or leeching of the antitoxic agent from the web. The same holds true for other downstream steps of the process. Co-owned Int'l. Pub. No. WO 2011/103578 to Messier, et al., entitled "Materials and Processes for Producing Antitoxic Fabrics" (the '578 publication), addresses these issues by providing methods of producing materials manufactured with higher concentrations of active antitoxic agent in the final product.

In particular, the '578 publication discloses various methods for producing an antitoxic material by introducing iodine into a nonwoven material at various multiple stages of production. In one embodiment, a nonwoven material is formed from polymer staple fibers with an iodinated resin embedded therein, and then subjected to immersion in a liquid or gas containing triiodide or triiodine prior to being dried. The additional post-processing immersion step was found to increase the amount of active antitoxic agent that can be incorporated into a fabric.

While the addition of an immersion step in the post-processing of the nonwoven was found to increase the amount of antitoxin in the product, and thus increase the measured kill performance, this additive step was also found to increase the amount of leaching and toxicity. In addition, the added immersion step increases the overall cost. Accordingly, a need still exists for a method of producing fibers and fabrics exhibiting increased antitoxin load capacity and efficacy over time combined with reduced levels of toxicity. Further reduction of the manufacturing cost resulting from wasted antitoxin in the manufacturing process is also desired.

SUMMARY

The present disclosure provides cost-effective materials and efficient manufacturing processes for manufacturing fibers and fabrics formed therefrom, particularly wovens and nonwovens, containing antitoxins. The resultant fabrics exhibit advantageous properties such as increased antitoxin load capacity and efficacy combined with reduced levels of toxicity. In addition, the material exhibits increased performances both over time of uses and after aging. The disclosure also provides products comprising the inventive antitoxic fibers and fabrics, such as: articles of clothing, cloth, tape, particularly health care related tape, wound dressings, gowns, surgical drapes, protective clothing, shoe covers, gloves, hair covers, air filters, including facemasks, privacy curtains, medical tape, hygienic products and wipes. In particular embodiments, a commercially available product from this list of products, whether previously treated with an antitoxin or not, can be treated according to the methods of the present disclosure to provide, for example, articles of clothing, cloth, a tape, wound dressing, gown, surgical drape, article of protective clothing, shoe cover, gloves, hair cover, air filter, including a facemask, privacy curtain, hygienic products or wipe with antitoxic or improved antitoxic properties.

In particular, the methods of the present disclosure significantly increase the amount of active antitoxic agent that can be loaded or impregnated into a fiber and fibrous media formed therefrom in a single manufacturing step. In some embodiments, the antitoxin may be impregnated on and into the fibrous material by molecular grafting. The resultant fibrous media exhibit both high efficacy and low toxicity. In addition, the manufacturing process is simplified and the amount of antitoxin lost during the process is advantageously reduced.

In one aspect, a process for producing an antitoxic fabric includes: providing a fibrous media comprising a non polymeric or a polymeric material; forming a dipping solution comprising a concentrate of at least one antitoxin and an additive portion, the additive portion including at least one of an anionic, cationic or nonionic component, an oil and/or an organic solvent, and an alcohol; fully immersing said media in said dipping solution to form a wet media; processing the wet media through rollers; and drying the wet media and isolating the fabric therefrom.

In another aspect, a process for producing an antitoxic fabric includes: providing a fibrous media comprising a non polymeric or a polymeric material and a spin finish; forming a concentrate of at least one antitoxin; fully immersing the media in the concentrate; mixing chemical components derived from the spin finish of the immersed fibrous media with the concentrate to form a dipping solution, wherein the chemical components include at least one of an anionic, cationic or nonionic component, an oil and/or an organic solvent, and an alcohol; continuing immersing the media in the dipping solution to form a wet media with impregnated material comprising the at least one antitoxin; processing the wet media through rollers; and drying the wet media and isolating the fabric therefrom.

The drying is preferably performed at a temperature of 90 degrees C. or below.

In another aspect, an antitoxic fabric is formed according to this dipping process. In additional aspects, an article of clothing, cloth, a wound dressing, tape, surgical drape, privacy curtain, facemask, gown, article of protective clothing, shoe covering, gloves, hair covering, air filter, hygienic product, medical tape, filter, or wipe includes the antitoxic fabric so formed.

In certain aspects, the at least one antitoxin includes triiodide. In additional aspects, the at least one antitoxin can also include an active agent selected from the group consisting of iodine, bromine, chlorine and hydrogen peroxide.

In one aspect of the present disclosure, an antitoxic fiber includes impregnated material containing an antitoxin, and additional chemical components, wherein the impregnated material is at least 1.0% by weight of the fiber, and the impregnated material includes an antitoxin and other additive chemical components.

In an additional aspect, the impregnated material of the antitoxic fiber is in an amount of about 1.3% to about 2.5% by weight of the fiber.

In another aspect, the antitoxin is in an amount of at least 0.1% by weight of the fiber.

In yet additional aspects, the additive chemical components include at least one of an anionic, cationic or nonionic component, an oil and/or an organic solvent, and an alcohol.

BRIEF DESCRIPTION OF THE DRAWINGS

FIG. 1 is a table of results of antimicrobial efficacy measured in accordance with ASTM 2149 testing methods for a surgical curtain formed by a method of the present disclosure compared to the antimicrobial efficacy measured for two commercially available surgical curtains. FIG. 1 provides data for contact times of 5 minutes and 15 minutes for three gram-negative bacteria *A. baumannii, P. aeruginosa*, and *S. enterica*.

FIG. 2 is a summary table of results of antimicrobial efficacy measured in accordance with ASTM 2149 testing methods for a surgical curtain formed by a method of the present disclosure compared to the antimicrobial efficacy measured for two commercially available surgical curtains for the gram-negative bacteria listed in FIG. 1, as well as for various gram-positive bacteria, *C. difficile* bacterial spores, and for the Influenza A H1N1 virus.

FIG. 3 is a table of results of antimicrobial efficacy measured over time of use for a facemask of the present disclosure and a prior art face mask.

FIG. 4 is a table of results of antimicrobial efficacy measured after speed aging for a facemask of the present disclosure and a prior art facemask.

FIGS. 5-7 are results of AATCC 100 tests of a media for use in a shower curtain formed in accordance with the present disclosure.

FIG. 8 describes the species of iodine on the antitoxin media tested in FIGS. 5-7.

FIG. 9 describes the effect of different rolling speeds in manufacturing the antitoxin media on the efficacy.

DETAILED DESCRIPTION OF EMBODIMENTS

The following sections describe exemplary embodiments of the present disclosure. It should be apparent to those skilled in the art that the described embodiments of the present disclosure provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present disclosure as defined herein and equivalents thereto.

Throughout the description, where items are described as having, including, or comprising one or more specific components, or where processes and methods are described as having, including, or comprising one or more specific steps, it is contemplated that, additionally, there are items of the present disclosure that consist essentially of, or consist of, the one or more recited components, and that there are processes and methods according to the present disclosure that consist essentially of, or consist of, the one or more recited processing steps.

It should be understood that the order of steps or order for performing certain actions is immaterial, as long as the embodiment remains operable. Moreover, two or more steps or actions may be conducted simultaneously.

Scale-up and/or scale-down of systems, processes, units, and/or methods disclosed herein may be performed by those of skill in the relevant art. Processes described herein are configured for batch operation, continuous operation, or semi-continuous operation.

In a method of the present disclosure, an antitoxin is impregnated to fibers and media formed therefrom in high concentrations through immersion of the media in a dipping solution which includes a concentrate of antitoxin. In some embodiments, the antitoxin may be impregnated on and into the fibrous material by molecular grafting. The resultant fabrics exhibit both superior efficacy and negligible toxicity.

Moreover, the manufacturing process of the disclosure is drastically simplified and less costly compared to known methods of manufacturing antitoxic materials.

An antitoxic fiber and fibrous media of the present disclosure include impregnated material preferably of at least 1.0% by weight of the fibrous material, where the impregnated material includes an antitoxin and other additive chemical components, the other additive chemical components preferably comprising components of a spin finish.

In additional embodiments, the impregnated material can comprise about 1.0% to about 3.5%, or, preferably, about 1.3% to about 2.5%, by weight of the fibrous material.

The impregnated material of a fiber or fibrous media of the present disclosure preferably includes antitoxin in an amount of at least 0.1% by weight of fibrous material. In one embodiment, the antitoxin is in an amount of from about 0.05% to about 20%. In another embodiment, the antitoxin is in an amount of from about 0.2% to about 10%. In still another embodiment, the antitoxin is in an amount of from about 1.0% to about 3.0%. In yet another embodiment, the antitoxin is in an amount of from about 5.0% to about 15%.

The other additive chemical components of the impregnated material preferably include one or more of an anionic, cationic or nonionic component, an oil, an organic solvent, and an alcohol. The components may be present individually or in combination.

Still other additive chemical components can include one or more of a preservative, emulsifier, anti-oxidants, pigments, adhesive, lubricant, and antifoam agents.

The total combined additive chemical components of the impregnated material are preferably in an amount totaling from about 0.01% to about 10% by weight of the fibrous material. In another embodiment, the other additive chemical components are in an amount from about 0.01% to about 7%.

In additional embodiments, the antitoxin is in an amount of at least four times, and more preferably, at least six times that of the combined additional chemical components by weight of the fibrous material.

It should be understood that the percentages of the various components by weight of fibrous material provided above are based on a treated, dried, fiber or fibrous media with no water.

In particular embodiments, the impregnated material is introduced to the fiber or fibrous media by dipping the fibrous material in a dipping solution according to the methods of the present disclosure.

In still additional embodiments, wherein a starting fiber is impregnated with the antitoxin-containing impregnated material through a dipping process, such as described herein, the antitoxin agent in the impregnated material before drying the media can range from about 40% w/w to 95% w/w and the remaining additive chemical components can range from about 5% w/w to 60% w/w of the total additive.

The manufacturing process of the present disclosure can be performed on most commercially available products formed from any woven or nonwoven, formed by any process (e.g., spunbond or meltblown). In particular embodiments, the method of the present disclosure can be applied as a post-treatment of any fibrous media, whether or not it was treated during the manufacturing process with an antitoxin.

The following examples, while limited to impregnating iodine into and onto the fibrous media from triiodide in the dipping solution, are not intended to necessarily be limited to any one antitoxin.

As used herein, triiodide refers to the triiodide ion, $I_3^-$, a polyatomic anion composed of three iodide atoms.

Additional antitoxins contemplated for use in place of, or in addition to, iodine include, but are not limited to, bromine, chlorine, fluorine, hydrogen peroxide, silver or silver nitrate, copper or copper nitrate, zinc, and triclosan.

In further embodiments, additional active agents or antitoxins can be added alone or in combination with iodine molecule depending on the desired performance of the fabric produced. Such agents include but are not limited to ethanol, 1-propanol, 2-propanol, isopropanol, cationic surfactant (e.g., benzalkonium chloride, chlorhexidine, octenidine dihydrochloride), metals, a quaternary ammonium compound (e.g., benzalkonium chloride (BAC), cetyl trimethylammonium bromide (CTMB), cetylpyridinium chloride (Cetrim, CPC), benzethonium chloride (BZT), chlorhexidine, octenidine), boric acid, brilliant green, chlorhexidine gluconate, mercurochrome, manuka honey, octenidine dihydrochloride, phenol (carbolic acid), sodium chloride, sodium hypochlorite, calcium hypochlorite, terpenes, or poly-hexamethyl-biguanide (PHMB) or mixtures thereof.

The fibrous media of the present disclosure can be formed of a polymeric or non polymeric material and can be produced by any method known in the art, including those described herein. In one embodiment, the media is formed of polymeric fibers, which can be formed into a thermally bonded media, for example, by extrusion and carding methods. The fibers may have hydrophobic properties.

In certain embodiments, a material for forming the fibrous media contains polyolefin, such as polypropylene, polyethylene and blends thereof. Other materials contemplated include any non polymeric and polymeric materials, both synthetic and nonsynthetic, known in the art, including but not limited to cotton, rayon, polyamide, nylon, PVC, and EMAC, and blends thereof. In addition, the fibers can be formed from a melt that contains, in addition to polymeric material, various other additives known in the art, such as calcium stearate, antioxidants, stabilizers, and so on.

In various embodiments, the fibrous media is a nonwoven formed from a 50/50 blend of polypropylene and synthetic cellulose acetate or alginate fibers having iodine molecularly grafted thereto from an immersion in the dipping (triiodide) solution.

A particularly preferred antitoxic nonwoven media is formed from a 50/50 blend of (spunbond) polypropylene and synthetic cellulose acetate fibers dipped in the triiodide solutions of the present disclosure. Another particularly preferred antitoxic nonwoven media is formed from a 50/50 blend of (spunbond) polypropylene and alginate fibers dipped in triiodide solution. Products, particularly wound dressings and antimicrobial tape, incorporating this antitoxic nonwoven are within the scope of this disclosure. Such wound dressings exhibit superior qualities over known dressings such as Silver-based dressings as well as other iodine dressings formed by other means.

The medical tape can also include an adhesive liner.

In another embodiment, a fabric or fibrous media of the present disclosure is formed of any fibers, and by any process (e.g., meltblown or spunbond process), capable of absorbing triiodide from the dipping solution, formed as described below, to obtain a high concentration of iodine in the fiber, while exhibiting negligible or immeasurable leaching.

In various embodiments, fibers and media formed therefrom of the present disclosure are characterized by a melt flow index (MFI) of at least 5 MFI. In another embodiment, the MFI is no more than 200 MFI, preferably 150 MFI. In yet another embodiment, the fibers are characterized by a melt flow index (MFI) of between about 50 and about 150 MFI. In still another embodiment, the fibers are characterized by a melt flow index (MFI) of between about 5 and about 50 MFI.

In a method of the present disclosure, the concentrate of the antitoxin in a dipping solution is adjusted to appropriate levels to obtain the desired concentration in the fabric. The optimum concentration of the antitoxin in the dipping solution will depend on the properties of the fibrous material that affect its ability to absorb the antitoxin of interest. One of skill in the art will understand that various processing properties can also be adjusted to optimize the absorption of the antitoxin so that the required concentration of antitoxin in the dipping solution to achieve can be minimized. In this way, a cost efficient process can be achieved with minimal waste product produced.

In one embodiment of a method of the present disclosure, antitoxin media are formed by dipping a (polymeric or nonpolymeric) fibrous media in a dipping solution containing a concentrate of the antitoxin in a sufficient amount to impregnate the antitoxin within and on the fibrous materials. The remaining portion of the dipping solution includes additive chemical components as described herein.

The dipping solution is preferably applied after formation of the fibrous media, for example, after crimping and processing fibers into a thermally bonded media, but may also be applied directly to the fibers after being formed.

As one of skill in the art will appreciate, there are many different species of iodine. The inventors discovered that for the media formed in accordance with the methods of the present disclosure, at least $I_2$, $I_3^-$, HOI, $I^-$, and $IO_3^-$ are formed on the media after immersion in the concentrated antitoxin solution in a proportion where the iodine active is in a majority versus the other species. To test the media, the molecularly grafted material was cut into swatches of 1"×1" and added to a 10 ml test tube of water. The sample was vortexed for 30 seconds before being analyzed on a spectrophotometer for each of the above species with a specific method for each. In this way, the amount in ppm of each species present could be determined. The inventors also observed that when air is passed through the media over a period of time, of 8 hours, for example, the media color changes from yellow to a light yellow. It was determined that the color change occurs as the species equilibrium shifts away from the $I_2$ towards the iodate and others, as the active iodine is released. When air is no longer flowing through the media, the yellow color comes back and the shift towards $I_2$ and less of the non active species like iodate and iodide.

The immersion step can be performed by dipping or immersing the media in the dipping solution for a period of time sufficient to achieve the desired concentration. The time of immersion may be a few seconds up to minutes, depending on the material, the concentration of the antitoxin in solution, and the desired resultant concentration in the fabric. It will be clear to one of ordinary skill in the art that the desired concentration in the fibers can be obtained by either increasing the immersion time, increasing the temperature of the dipping fluids or the concentration of the antitoxin in solution, or with an optimal combination of these parameters, depending on manufacturing needs. The dipping solution is preferably maintained at about room temperature, or in a temperature range of from about 20° C. to about 25° C. The temperature can be adjusted above this range as appropriate to obtain the desired impregnation of antitoxin in the media, keeping low enough to avoid degradation of the antitoxin and other dipping solution components.

In a preferred embodiment, the antitoxin in the dipping solution includes tri-iodide. The tri-iodide is of a concentration of at least 400 ppm of iodine, preferably at least about 2500 ppm of iodine and preferably less than or equal to about 100,000 ppm. In one embodiment, the tri-iodide is between about 1,000 ppm and about 10,000 ppm, preferably, between about 5000 ppm and 10,000 ppm iodine.

The method of the present disclosure includes immersion of the selected fibrous media described above in a dipping solution characterized by a high concentration of iodine, preferably of at least 1000 ppm. By itself, the addition of iodine to an aqueous solution can result in a maximum of only about 330 ppm. Because a higher concentration is desired to maximize the loading of the antimicrobial in the fibers, potassium iodide is preferably added and mixed with the iodine in the water or other solvent to first form a triiodide solution, which is then added to the remainder of the dipping solution. The potassium iodide assists in converting the diatomic iodine to triiodide ions, resulting in concentrations over the approximately 330 ppm that can be achieved by adding solid iodine alone. Concentrations of up to 5000 ppm, and higher, close to saturation levels, are achieved by mixing iodine and potassium iodide to permit the iodine concentration to rise to the desired levels.

For example, a concentrated triiodide solution (1 Normal) of about 129,600 ppm of iodine is achieved by adding potassium iodide. This solution is then diluted to the desired optimal levels.

An example of the preparation of the concentrated triiodide solution before dilution and addition to the remainder of the dipping solution is provided in Example 1 below.

The other additive chemical components added to the antitoxin in the dipping solution preferably include one or more of an anionic, cationic or nonionic component, an oil, an organic solvent, and an alcohol. The components may be present individually or in combination.

The dipping solution can optionally also include one or more of a preservative, emulsifier, anti-oxidants, pigments, adhesive, lubricant, and antifoam agents in an amount sufficient to enhance impregnation of the antitoxin in the media.

In one embodiment, the antitoxin in the impregnated material in the resultant antitoxic fiber or fibrous media is preferably in similar proportion as in the dipping solution.

The dipping process can be controlled by unwinding a fibrous media, for example, a thermally bonded media as described herein, and dipping the media in the dipping solution comprising an antitoxin, preferably tri-iodide, of desired concentration. The dipping process is executed to achieve a desired contact time of the media with the antitoxin by controlling both contact time, temperature, and concentration of the antitoxin solution that comes into contact with the media. The process can be achieved by continuous unwinding and re-winding the media in the antitoxin, e.g., tri-iodide, dipping solution or by dipping a specific length of media in the dipping solution with no movement (static) for a period of minutes. In each case, the parameters of contact time in the bath and concentration of tri-iodide are controlled.

After dipping, the media is dried by appropriate means, such as by passing the treated media through rollers to squeeze out excess liquid and then passing it into an oven for a few seconds to minutes depending on the presence of humidity. The rollers also aid in forcing the antitoxin molecules to penetrate into the media. The drying temperature is preferably between about 20° C. and 85° C. for a reasonable residence time in the oven, preferably for a humidity measure which smaller than about 10%.

Exceeding 85° C. is generally undesirable as this will cause an evaporation/loss of the bound tri-iodide and initiate a loss of activity of the media as measured by the iodine leaching from the media. One of skill in the art will appreciate that a combination of drying time and temperature can be optimized for the particular media and antitoxin.

By applying the method described herein, fibrous media or fabrics with antitoxic properties can be produced. The fabrics can be processed from either wovens or nonwovens formed by a weaving, spunbond, meltblown, or other process. The antitoxic properties are imparted to the fabric by introducing an active agent, such as an antimicrobial agent, to the fabric by immersion in a dipping solution that includes a concentration of antitoxin and appropriate additives described herein. The fabrics produced in accordance herewith have widespread utility. For instance, they can be used as articles of clothing, cloth, medical tape, wound dressings, gowns, drapes, air filters, protective clothing, shoe coverings, gloves, hair coverings, privacy curtains, facemasks, and wipes.

For example, a privacy or surgical curtain of the present disclosure, which can be a disposable curtain, includes at least one layer of antitoxic media formed in accordance with the methods described herein. In one embodiment, the antitoxic layer is a non-woven spunbond material formed of polypropylene, which is immersed in a triiodide solution formed in accordance with the present disclosure, including 8500 ppm iodine.

As described and shown in FIGS. 1-2, the treatment of hospital curtain fabrics in accordance with the method of the present disclosure exhibits strong antibacterial efficacy against gram-negative bacteria such as *Pseudomonas aeruginosa*, *A. baumannii*, and *S. enterica*, gram-positive bacteria such as *Staphylococcus aureus* MRSA, and *E. faecalis* VRE after an exposure time of 5 minutes. Furthermore, stability testing performed under speed aging conditions indicated that the antimicrobial efficacy of the treated curtain material is maintained over time.

In particular, FIG. 1 is a table of results of antimicrobial efficacy measured in accordance with ASTM 2149 testing methods for a surgical curtain formed by a method of the present disclosure compared to the antimicrobial efficacy measured for two commercially available surgical curtains. FIG. 1 provides data after the surgical curtain is contacted for 5 minutes and 15 minutes, as shown in the table, with each of three gram-negative bacteria: *A. baumannii*, *P. aeruginosa*, and *S. enterica*.

FIG. 2 is a summary table of results of antimicrobial efficacy measured in accordance with ASTM 2149 testing methods for a surgical curtain formed by a method of the present disclosure compared to the antimicrobial efficacy measured for two commercially available surgical curtains for the gram-negative bacteria listed in FIG. 1, as well as for various gram-positive bacteria, *C. difficile* bacterial spores, and for the Influenza A H1N1 virus. The table lists results after contact times of at least 5 minutes with the listed toxin, after 15 minutes for Influenza A H1N1 and after 24 hours of exposure to bacterial spores.

It should be clear that any other product containing a similarly formed antitoxic layer of a non-woven spunbond polypropylene material will have substantially similar excellent antibacterial efficacy and stability over time.

In a particular embodiment, a tape, particularly a medical or surgical tape, is formed of a nonwoven breathable cotton or other fibrous media, dipped in a dipping solution including an antimicrobial in accordance with the methods of the present disclosure. In one embodiment, the antimicrobial is triiodide. Additional antitoxins can also be included in the dipping solution.

In other embodiments of a medical, hygienic or surgical tape, the fibrous media is treated during formation of the fibrous media with an antitoxin, for example, a metal such as zinc oxide, before the additional dipping process of the present disclosure to add additional antitoxin. Preferably, the fibrous media, which may or may not contain an antitoxin, is immersed in a dipping solution including a concentrate of triiodide. The tape also includes an adhesive surface which preferably includes an iodophobic and/or halogen-containing adhesive such as fluorine. Accordingly, the iodine will preferentially absorb into nonadhesive surfaces of the tape.

It has surprisingly been found that by adding a relatively small amount of additive chemical components as described to a dipping solution, which includes an antitoxin in an appropriate concentration by weight of the fibrous material, superior loading of the antitoxin to the fibrous material is achieved, resulting in stable and high efficacy fibers and fibrous media. The additive components include at least one or more of a surfactant, an anti-static agent, an oil and/or organic solvent, and an alcohol. Moreover, the manufacturing process can be applied to any woven or nonwoven media.

In one embodiment, the concentration of antitoxin as well as the amount of chemical components in the dipping solution can be monitored and the amount of the individual components quantified throughout the impregnation process. The amounts can then be adjusted during the process and in subsequent dippings to optimize the absorption and impregnation of the antitoxin in the fiber and reduce the waste product remaining.

Example 1

Preparation of Triiodide Solution for Mixing into Dipping Solution

A. Prepare 1N iodine (129,600 ppm $I_2$):
1. In a 1 L volumetric flask, add approx 250 mL high purity water
2. Weigh out 175 g of KI solid and add to the 1 L flask containing the water
3. Swirl solution in flask to dissolve all KI.
4. Weigh out 130 g of Iodine solid and add to the 1 L flask containing the KI and water solution
5. Fill the volumetric flask with high purity water to the marked line
6. Add a magnetic stir bar to the flask
7. Cap the flask with a glass stopper
8. Cut a piece of parafilm and wrap it around the top of the flask/stopper to prevent any leakage
9. Take the flask and place it on a magnetic stir plate.
10. Set stir control to 7 and let the solution mix overnight to dissolve all iodine solid
11. Dilute according to needs Example 2

Example of an Antitoxic Fibrous Media

In one example, a sample size (18.0 g) of an antitoxic fibrous media of a polyolefin containing iodine was formed by the method of the present disclosure, including dipping the starting polyolefin in a concentrated solution of triiodide of about 8500 ppm. The water content constituted approximately 5.0% of the weight so that after drying, the about 17.10 g of dry antitoxic media is produced. In this dry media weight, the % of total impregnated material added to the untreated sample was measured to be in the range of about 1.6% or 0.274 g. The antitoxin agent, iodine, was measured at about 0.248 g. or 1.45% by weight of the dry antitoxic media. The additive chemical components constituted about 0.026 g.

A second sample size (18.0 g) of an antitoxic fibrous media of a polyolefin containing iodine, was prepared in accordance with the same method as sample one. The initial water content before drying was approximately 2.5% of the starting weight to produce about 17.60 g of dry antitoxin fibrous media. In this media weight, the % of total impregnated material was measured to be about 1.6% or 0.282 g. The antitoxin agent was measured at about 0.248 g or 1.41% by weight of the dry antitoxic media and 0.034 g is made out of other components.

Example 3

Example of a Facemask

A facemask formed with an antitoxic fibrous media of the present disclosure

Referring to FIG. 3, a fibrous layer for a facemask was treated with a tri-iodide dipping solution prepared in accordance with a method of the present disclosure. The resulting fibrous media was utilized to make a scrim layer for a face mask. The scrim is termed TrioMed Active scrim, and the prior art scrim is referred to as Triosyn/Simalfa in the figure. The TrioMed active scrim contains 0.4 grams per square meter (GSM) of iodine. The Triosyn/Simalfa scrim contains 2.0 GSM of iodine.

The bacteriocidal efficacy of these masks was tested by incubating each test mask with a known amount of *Pseudomonas aeruginosa* for 15 minutes. The number of live bacteria remaining was then quantified.

The freshly produced Triosyn/Simalfa and Triomed masks were tested for their ability to kill bacteria. The prior art mask demonstrated a 3.77 log reduction in bacteria, and the Triomed Active scrim demonstrated greater than 4.92 log reduction in bacteria, a 10× improvement over the prior art mask.

Each mask was then placed on an apparatus to simulate breathing for 6 hours and then their ability to kill bacteria was tested. The Triosyn/Simalfa mask exhibited 0.59 log reduction in bacteria, whereas the Triomed mask exhibited a greater than 4.92 log reduction. In summary, the Triomed mask exhibited a sustained ability to kill bacteria after 6 hours of simulated use that far exceeds the performance of the prior art mask, even though the mask formed in accordance with the present disclosure contains five (5) times less iodine concentration.

Referring to FIG. 4, each of the Triosyn/Simalfa and Triomed masks were also tested after aging for 2 months at room temperature. The Triosyn/Simalfa masks exhibited a 0.52 log reduction in bacteria, and the Triomed masks exhibited a 4.66 log reduction in bacteria after aging. Accordingly, a facemask including the fibrous media of the present disclosure exhibits an increased resistance to degradation over time, as compared to the prior art facemask, with far less iodine concentration.

In one embodiment of a method of the present disclosure, a commercially available polyolefin fiber or fibrous media is impregnated with an antitoxin such as iodine. Such commercial fibers and media, whether formed in a spunbond or meltblown process, are formed with a spin finish that generally includes at least an oil and an antistatic agent, which can be anionic, cationic, or nonionic. During the process of dipping the fiber or fibrous media in a dipping solution of the present disclosure, some of the spin finish is stripped off into the dipping solution. Accordingly, the dipping solution can include a concentrate of an antitoxin, as described herein, and additive chemical components from the spin finish of the fibrous material, which are continually mixed with the antitoxin. The components of the dipping solution can be monitored throughout the dipping process and additional chemical components, as described herein, can be added as necessary to maintain an optimum composition for impregnation of the antitoxin into the fibers throughout the manufacturing process.

Such a process was applied to a commercial spunbond polyolefin fiber having a spin finish in an amount approximately 0.18% by weight of the polyolefin fiber. In particular, the starting fibrous material was dipped in a concentrate to triiodide of about 8500 ppm. As the additive components from the spin finish were removed from the fibers and entered the dipping solution, they were circulated and maintained in the dipping solution.

A blank (untreated) starting media had an initial weight of about 19.4 grams, of which 34.8 mg (0.18%) was measured as spin finish. The organic components of the spin finish were analyzed before treatment with the triiodide solution and found to contain primarily:

Coconut fatty acids ethoxylated with about 9 moles of ethylene oxide, >=90% of the spin finish Phosphate ester made from an ethoxylated fatty alcohol, about 5%

Triethanolamine, 2-3% and a small amount of water.

A second sample of the same starting commercial fiber was treated in accordance with the method of the disclosure, by dipping in a dipping solution with about 8000-8500 ppm, to produce an antitoxin-treated fabric. In this instance, the original spin finish components that were stripped from the starting fiber were circulated through the dipping solution, and not filtered out. The treated fabric, which was about 18.5 grams, was then dried in an oven at or below 85 C and analyzed for content. About 298 mg of the treated fabric, or about 1.61% by weight of the fibrous material, constituted the impregnated material which included spin finish components and iodine, of which 1.5% was iodine and 0.11% were other chemical components from the spin finish of the starting material.

Methods of dipping commercial fibrous media in a concentrate of triiodide solution were also performed in which the spin finish that entered the dipping solution was continually filtered out. It was surprisingly found that while the amount of iodine in the finished product was substantially the same as in the method described above, the resultant treated fabric performed poorly, particularly over a short aging time.

As shown by examples provided herein, the method of the present disclosure, which maintains components found in spin finish in the antitoxin-containing dipping solution, provide an antitoxic fibrous media with superior efficacy, lower toxicity, and better performance over time.

Regardless of the type of fibrous media used, the various polymers for forming non-woven and woven media, such as polypropylene, polyester, polyamide, cellulose, and so on, are known to be hydrophobic in nature. Accordingly, the molecular grafting with triiodide, and absorption of any type of liquid, is very difficult by nature, including for both low and high Melt Flow Index (MFI) fibers, whether non-woven or woven.

The inventors have surprisingly discovered that the hydrophobic nature of the polymers is efficiently transformed into a hydrophillic nature by adding components of a spin finish to the grafting antitoxin (triiodide) solution, or, optionally, the fibrous media is immersed in the antitoxin solution and in a spin finish in two separate steps, the antitoxin solution and the spin finish being provided in two separate vessels. As one of skill in the art will appreciate, spin finish is an oily surfactant solution that is used as a fiber coating to ensure that fibers do not rub together and affect the alignment of the fibers due to a static charge build up. In various embodiments, the spin finish components can include, but are not limited to, a glycol, such as Polyethylene Glycol (PEG), an amine base product, such as triethanolamine, and/or an ester, such as a phosphate ester, or any other ester type chemical with or without anti-static agent.

In one embodiment, the spin finish components include a glycol component of at least 10-95% weight/weight, triethanolamine of between about 0.1 to about 5% weight/weight, and an ester of between about 1% and about 5% weight/weight. The spin finish components are provided in sufficient proportions to promote grafting of triiodide onto the media matrix and stabilizing the active compound within the fibers.

Referring to FIGS. 5-7, a standard AATCC test method was applied to test the antimicrobial properties of a privacy curtain comprising a layer of the antitoxic fibrous media of the present disclosure under different conditions. The antimicrobial-treated swatch was exposed to a microbial suspension for 15 minutes. The swatch is then placed in a neutralizing fluid to recover viable microorganisms (colonies), which are then counted and recorded as CFU, in accordance with the AATCC 100 standard. The results of exposure to various microorganisms for different conditions and for various media are shown.

FIG. 5 are the results of testing a hydrophilic media formed of a spunbond meltblown 100% polypropylene with a spin finish coating. The media was immersed in a triiodide solution of about 7000 ppm iodine comprising spin finish components as described above in an amount of about 3% w/w. The results measured after aging to 25 days are shown.

FIG. 6 are the results of testing a hydrophobic media formed of a spunbond meltblown 100% polypropylene without a spin finish coating. The media was immersed in a triiodide solution of about 7000 ppm iodine comprising spin finish components as described above in an amount of about 3% w/w. The results measured after aging to 25 days are shown. Using the components of a spin finish in the dipping solution transforms the fibrous media to have hydrophilic properties.

FIG. 7 shows results of a "wet glove" test, where the iodine is attempted to be removed with contact with the glove. It was shown that iodine does not come off of the media formed in accordance with FIG. 6 when tested with the wet glove.

FIG. 8 shows an iodine species analysis of a fibrous media formed in accordance with the methods of the present disclosure, accounting for the observed color shift of the media when exposed to bacteria.

FIG. 9 describes the results of a challenge to exposure of the media to *P. Aeruginosa* for the treated media described in FIG. 6, manufactured at varying roll speeds.

It should be apparent to those skilled in the art that the described embodiments of the present disclosure provided herein are illustrative only and not limiting, having been presented by way of example only. As described herein, all features disclosed in this description may be replaced by alternative features serving the same or similar purpose, unless expressly stated otherwise. Therefore, numerous other embodiments of the modifications thereof are contemplated as falling within the scope of the present disclosure as defined herein and equivalents thereto.

What is claimed is:

1. An antitoxic fiber, the antitoxic fiber comprising a fiber formed of a polymeric or nonpolymeric material, and impregnated material impregnated into the fiber, the antitoxic fiber being characterized by a humidity measure of less than about 10%, wherein the impregnated material is at least 1.0% by weight of the antitoxic fiber based on dried fiber weight and includes at least one active antitoxin, wherein one of the at least one active antitoxin is triiodide, and additional chemical components, and wherein the additional chemical components include ethoxylated coconut fatty acids in an amount of 90% or more of the additional chemical components, phosphate ester formed from an ethoxylated fatty alcohol in an amount of about 5% of the additional chemical components, and triethanolamine in an amount between 2-3% of the additional chemical components, wherein the at least one active antitoxin, including the triiodide, impregnated with the additional chemical components is stabilized in the antitoxic fiber, the antitoxic fiber being efficacious on contact, and maintaining efficacy with negligible toxicity in use.

2. An antitoxic fabric formed from the antitoxic fiber of claim 1.

3. The antitoxic fiber of claim 1, wherein the impregnated material is in an amount of about 1.3% to about 2.5% by weight of the antitoxic fiber based on dried fiber weight.

4. The antitoxic fiber of claim 1, wherein the at least one antitoxin is in an amount greater than a total amount of the additional chemical components by weight of the antitoxic fiber based on dried fiber weight.

5. The antitoxic fiber of claim 1, wherein the at least one active antitoxin, including the triiodide, is in an amount of about 1.4% and the impregnated material is in a total amount of about 1.6% by weight of the antitoxic fiber based on dried fiber weight.

6. The antitoxic fiber of claim 1, wherein the additional chemical components further include at least one of a preservative, an emulsifier, an anti-oxidant, a pigment, an adhesive, a lubricant, and an antifoam agent.

7. The antitoxic fiber of claim 6, wherein the at least one active antitoxin is in an amount at least four times that of the additional chemical components by weight of the antitoxic fiber based on dried fiber weight.

8. The antitoxic fiber of claim 1, wherein the fiber is formed from at least one of a polypropylene and synthetic cellulose acetate and a blend thereof.

9. The antitoxic fiber of claim 1, wherein the fiber is formed of at least one of a polypropylene, a polyester, a polyamide, and a cellulose media.

10. The antitoxic fiber of claim 1, wherein the fiber is formed from at least one of cotton, rayon, polyamide, nylon, PVC, and EMAC, and blends thereof.

11. An article of clothing, cloth, wound dressing, tape, surgical drape, privacy curtain, facemask, gown, article of protective clothing, shoe covering, gloves, hair covering, air filter, hygienic product, or wipe comprising the antitoxic fabric of claim 2.

12. An antitoxic fabric formed of antitoxic fibers comprising fibers formed of a polymeric or nonpolymeric material and impregnated material impregnated into the fibers, wherein the impregnated material is at least 1.0% by weight of the antitoxic fibers based on dried fiber weight and includes at least one active antitoxin, wherein one of the at least one active antitoxin is triiodide, and additional chemical components, and wherein the additional chemical components include coconut fatty acids ethoxylated with ethylene oxide, phosphate ester formed from an ethoxylated fatty alcohol, and triethanolamine in sufficient proportion to stabilize the at least one active antitoxin, including the triiodide, in the antitoxic fibers and fabric, the antitoxic fabric being efficacious on contact and maintaining efficacy with negligible toxicity in use, and wherein a humidity measure of the antitoxic fabric is smaller than about 10%.

13. An article of clothing, cloth, wound dressing, tape, surgical drape, privacy curtain, facemask, gown, article of protective clothing, shoe covering, gloves, hair covering, air filter, hygienic product, or wipe comprising the antitoxic fabric of claim 12.

14. The antitoxic fabric of claim 12, wherein the coconut fatty acids ethoxylated with ethylene oxide is in an amount of at least 90% weight/weight of the additional chemical components.

15. The antitoxic fabric of claim 14, wherein the triethanolamine is in an amount of between 2-3% weight/weight of the additional chemical components, and the phosphate ester is an amount of about 5% weight/weight of the additional chemical components.

* * * * *